US006708048B1

(12) United States Patent
Chance

(10) Patent No.: US 6,708,048 B1
(45) Date of Patent: *Mar. 16, 2004

(54) PHASE MODULATION SPECTROPHOTOMETRIC APPARATUS

(75) Inventor: Britton Chance, Marathon, FL (US)

(73) Assignee: Non-Invasive Technology, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/229,284

(22) Filed: Jan. 13, 1999

Related U.S. Application Data

(63) Continuation of application No. 08/731,443, filed on Oct. 15, 1996, now Pat. No. 6,134,460, which is a continuation of application No. 08/031,945, filed on Mar. 16, 1993, now Pat. No. 5,564,417, which is a continuation-in-part of application No. 08/076,370, filed on Jun. 14, 1993, now Pat. No. 5,553,614, which is a continuation of application No. 07/645,590, filed on Jan. 24, 1991, now abandoned, which is a continuation-in-part of application No. 07/578,063, filed on Sep. 5, 1990, now Pat. No. 5,122,974, which is a continuation of application No. 07/307,066, filed on Feb. 6, 1989, now Pat. No. 4,972,331.

(51) Int. Cl.$^7$ .................................. A61B 1/00

(52) U.S. Cl. ................ 600/322; 600/310; 600/316; 600/326

(58) Field of Search .................... 600/310, 314, 600/316–324, 326

(56) References Cited

U.S. PATENT DOCUMENTS

| | | | |
|---|---|---|---|
| 3,229,685 A | 1/1966 | Ringkamp et al. | |
| 3,461,856 A | 8/1969 | Polanyi | |
| 3,638,640 A | 2/1972 | Shaw | |
| 3,866,599 A | 2/1975 | Johnson | |
| 4,029,085 A | 6/1977 | De Witt et al. | |
| 4,207,874 A | 6/1980 | Choy | |
| 4,223,680 A | 9/1980 | Jöbsis | |

(List continued on next page.)

FOREIGN PATENT DOCUMENTS

| | | |
|---|---|---|
| EP | 0 233 108 A1 | 8/1987 |
| EP | 0 467 459 A2 | 1/1992 |
| EP | 0 509 310 A2 | 10/1992 |
| WO | WO 90/04941 | 5/1990 |
| WO | WO 92/13598 | 8/1992 |
| WO | WO 92/20273 | 11/1992 |

OTHER PUBLICATIONS

European Search Report for European Patent Appln. No. 94911595.0 dated Sep. 17, 1998 (5 pp).

Chance et al., "Photon Migration in Muscle and Brain," *Photo Migration in Tissues*, Academic Press/New York, pp. 121–135, 1989.

Cui et al., "Experimental Study of Migration Depth for the Photons Measured at Sample Surface," *Proceedings of Time–Resolved Spectroscopy and Imaging of Tissues, SPIE*, 1413:180–191,1991.

(List continued on next page.)

Primary Examiner—David M. Shay
(74) Attorney, Agent, or Firm—Fish & Richardson P.C.

(57) ABSTRACT

A pathlength corrected spectrophotometer for tissue examination includes an oscillator for generating a carrier waveform of a selected frequency, an LED light source for generating light of a selected wavelength that is intensity modulated at the selected frequency introduced to a subject, and a photodiode detector for detecting light that has migrated in the tissue of the subject. The spectrophotometer also includes a phase detector for measuring a phase shift between the introduced and detected light, a magnitude detector for determination of light attenuation in the examined tissue, and a processor adapted to calculate the photon migration pathlength and determine a physiological property of the examined tissue based on the pathlength and on the attenuation data.

36 Claims, 5 Drawing Sheets

U.S. PATENT DOCUMENTS

| | | |
|---|---|---|
| 4,281,645 A | 8/1981 | Jöbsis |
| 4,416,285 A | 11/1983 | Shaw et al. |
| 4,648,892 A | 3/1987 | Kittrell et al. |
| 4,655,225 A | 4/1987 | Dähne et al. |
| 4,675,529 A | 6/1987 | Kushida |
| 4,700,708 A | 10/1987 | New, Jr. et al. |
| 4,773,422 A | 9/1988 | Isaacson et al. |
| 4,800,885 A | 1/1989 | JOhnson |
| 4,827,938 A | 5/1989 | Parker |
| 4,895,156 A | 1/1990 | Shulze |
| 4,908,762 A | 3/1990 | Suzuki et al. |
| 4,926,867 A | 5/1990 | Kanda et al. |
| 4,972,331 A | 11/1990 | Chance |
| 5,127,408 A | 7/1992 | Parsons et al. |
| 5,167,230 A | 12/1992 | Chance |
| 5,187,672 A | 2/1993 | Chance et al. |
| 5,197,470 A | 3/1993 | Helfer et al. |
| 5,242,438 A | 9/1993 | Saadatmanesh et al. |
| 5,257,991 A | 11/1993 | Fletcher et al. |
| 5,596,987 A * | 1/1997 | Chance ...................... 600/476 |
| 5,779,631 A * | 7/1998 | Chance ...................... 600/476 |

OTHER PUBLICATIONS

Lakowicz, "Gigahert Frequency–Domain Fluorometry: Resolution of Complex Intensity Decays, Picosecond Processes and Future Developments," *Photon Migration in Tissues*, pp. 169–185, 1989.

Sevick et al., "Analysis of absorption, scattering, and hemoglobin saturation using phase modulation spectroscopy," *Proceedings of Time–Resolved Spectroscopy and Imaging Tissues, SPIE*, 1431:264–275, 1991.

Sevick et al., "Photon migration in a model of the head measured using time–and frequency–domain techniques . . ." *Proceedings of Time–Resolved Spectroscopy and Imaging Tissues, SPIE*, 1431:84–96, 1991.

Sevick et al., "Quantitation of Time–and Frequency–Resolved Optical Spectra for the Determination of Tissue Oxygenation," *Analytical Biochemistry*, 195:331–351, 1991.

Weng et al., "Measurement of Biological Tissue Metabolism Using Phase Modulation Spectroscopic Technology," *Proceedings of Time–Resolved Spectroscopy and Imaging Tissues, SPIE*, 1431:161–170, 1991.

* cited by examiner

PHASE MODULATION SPECTROPHOTOMETRIC APPARATUS

CROSS REFERENCE TO RELATED APPLICATION

This is a continuation application of application Ser. No.: 08/731,443, filed Oct. 15, 1996 now U.S. Pat. No. 6,134,460, which is a continuation of application Ser. No.: 08/031,945, filed Mar. 16, 1993, now issued as U.S. Pat. No. 5,564,417, which is a continuation-in-part of application Ser. No. 08/076,370, filed Jun. 14, 1993, now issued as U.S. Pat. No. 5,553,614, which is a continuation of application Ser. No. 07/645,590, filed Jan. 24, 1991, now abandoned, which is a continuation-in-part of 07/578,063, filed Sep. 5, 1990, now issued as U.S. Pat. No. 5,122,974, which is a continuation of application Ser. No. 07/307,066, filed Feb. 6, 1989, now issued as U.S. Pat. No. 4,972,331, all of which are incorporated by reference as if fully set forth in their entireties herein.

This application is a continuation-in-part of application Ser. No. 07/645,590 filed Jan. 24, 1991 incorporated by reference as if fully set forth herein.

BACKGROUND OF THE INVENTION

The present invention relates to a wearable tissue spectrophotometer for in vivo examination of tissue of a specific target region.

Continuous wave (CW) tissue oximeters have been widely used to determine in vivo concentration of an optically absorbing pigment (e.g., hemoglobin, oxyhemoglobin) in biological tissue. The CW oximeters measure attenuation of continuous light in the tissue and evaluate the concentration based on the Beer Lambert equation or modified Beer Lambert absorbance equation. The Beer Lambert equation (1) describes the relationship between the concentration of an absorbent constituent (C), the extinction coefficient ($\epsilon$), the photon migration pathlength <L>, and the attenuated light intensity ($I/I_o$).

$$\frac{\log[I/I_o]}{<L>} = \sum \epsilon_i C_i \qquad (1)$$

The CW spectrophotometric techniques can not determine $\epsilon$, C, and <L> at the same time. If one could assume that the photon pathlength were constant and uniform throughout all subjects, direct quantitation of the constituent concentration (C) using CW oximeters would be possible.

In tissue, the optical migration pathlength varies with the size, structure, and physiology of the internal tissue examined by the CW oximeters. For example, in the brain, the gray and white matter and the structures thereof are different in various individuals. In addition, the photon migration pathlength itself is a function of the relative concentration of absorbing constituents. As a result, the pathlength through an organ with a high blood hemoglobin concentration, for example, will be different from the same with a low blood hemoglobin concentration. Furthermore, the pathlength is frequently dependent upon the wavelength of the light since the absorption coefficient of many tissue constituents is wavelength dependent. Thus, where possible, it is advantageous to measure the pathlength directly when quantifying the hemoglobin concentration in tissue.

SUMMARY OF THE INVENTION

In one aspect, the present invention is a pathlength corrected oximeter that utilizes principles of continuous wave spectroscopy and phase modulation spectroscopy. The oximeter is a compact unit constructed to be worn by a subject on the body over long periods of activity. The oximeter is also suitable for tissue monitoring in critical care facilities, in operating rooms while undergoing surgery or in trauma related situations.

The oximeter is mounted on a body-conformable support structure placed on the skin. The support structure encapsulates several light emitting diodes (LEDs) generating light of different wavelengths introduced into the examined tissue and several photodiode detectors with interference filters for wavelength specific detection. Since both the LEDs and the photodiodes are placed directly on the skin, there is no need to use optical fibers. The distance between the LEDs and the diode detectors is selected to examine a targeted tissue region. The support structure also includes a conformable barrier, located between the LEDs and the diode detectors, designed to reduce detection of light that migrates subcutaneously from the source to the detector. The support structure may further include means for preventing escape of photons from the skin without being detected; the photon escape preventing means are located around the LEDs and the photodiode detectors.

The LEDs, the diode detectors, and the electronic control circuitry of the oximeter are powered by a battery pack adapted to be worn on the body or by the standard 50/60 Hz supply. The electronic circuitry includes a processor for directing operation of the sources, the detectors and for directing the data acquisition and processing. The data may be displayed on a readout device worn by the user, sent by telemetry to a remote location or accumulated in a memory for later use.

The oximeter is adapted to measure the attenuation of light migrating from the source to the detector and also to determine the average migration pathlength. The migration pathlength and the intensity attenuation data are then used for direct quantitation of a tissue property.

In another aspect, the invention is a spectrophotometer for tissue examination utilizing a measured average pathlength of migrating photons, including an oscillator adapted to generate a carrier waveform of a selected frequency comparable to an average migration time of photons scattered in tissue on paths from an optical input port to an optical detection port; a light source, operatively connected to the oscillator, adapted to generate light of a selected wavelength that is intensity modulated at the frequency and introduced to a subject at the input port; a photodiode detector adapted to detect, at the detection port, light of the selected wavelength that has migrated in the tissue of the subject between the input and detection ports; a phase detector, operatively connected to receive signals from the oscillator and the diode detector, adapted to measure a phase shift between the introduced and the detected light; and a processor adapted to calculate pathlength based on the phase shift, and determine a physiological property of the examined tissue based on the pathlength.

In another aspect, the invention is a spectrophotometer for tissue examination utilizing a measured average pathlength of migrating photons, including an oscillator adapted to generate a carrier waveform of a selected frequency comparable to an average migration time of photons scattered in tissue on paths from an optical input port to an optical detection port; a light source, operatively connected to the oscillator, adapted to generate light of a selected wavelength that is intensity modulated at the frequency and introduced to a subject at the input port; a photodiode detector adapted to detect, at the detection port, light of the selected wavelength that has migrated in the tissue of the subject between the input and detection ports; a phase splitter adapted to produce, based on the carrier waveform, first and second reference phase signals of predefined substantially different phase; first and second double balanced mixers adapted to correlate the reference phase signals and signals of the detected radiation to produce therefrom a real output signal and an imaginary output signal, respectively; and a processor adapted to calculate, on the basis of the real output signal and the imaginary output signal, a phase shift between the introduced light and the detected light, and determine a physiological property of the examined tissue based on the phase shift.

In another aspect, the invention is a spectrophotometer for tissue examination utilizing a measured average pathlength of migrating photons, comprising a first oscillator adapted to generate a carrier waveform of a first selected frequency comparable to an average migration time of photons scattered in tissue on paths from an optical input port to an optical detection port; a light source, operatively connected to the oscillator, adapted to generate light of a selected wavelength, intensity modulated at the first frequency, that is introduced to a subject at the input port; a photodiode detector adapted to detect, at the detection port, light of the wavelength that has migrated in the tissue of the subject between the input and detection ports, the detector producing a detection signal at the first frequency corresponding to the detected light; a second oscillator adapted to generate a carrier waveform of a second frequency that is offset on the order of $10^4$ Hz from the first frequency; a reference mixer, connected to the first and second oscillators, adapted to generate a reference signal of a frequency approximately equal to the difference between the first and second frequencies; a mixer connected to receive signals from the second oscillator and the detection signal and adapted to convert the detection signal to the difference frequency; a phase detector, operatively connected to receive signals from the reference mixer and the converted detection signal, adapted to measure a phase shift between the introduced light and the detected light; and a processor adapted to calculate the pathlength based on the phase shift, and to determine a physiological property of the examined tissue based on the pathlength.

Preferred embodiments of these aspects may include one or more of the following features.

The spectrophotometer may further include a magnitude detector, connected to the photodiode detector, adapted to measure magnitude of the detected light, and the processor is further adapted to receive the magnitude for determination of the physiological property.

The spectrophotometer may further include a low frequency oximeter circuit, switchably connected to the source and the photodiode, adapted to determine absorption of light at the wavelength; and the processor is further adapted to receive absorption values from the oximeter circuit for determination of the physiological property.

The spectrophotometer may further include two automatic gain controls adapted to level signals corresponding to the introduced light and the detected light, both the leveled signals being introduced to the phase detector.

The photodiode detector may further include a substantially single wavelength filter.

The spectrophotometer may further include a second light source, operatively connected to the oscillator, adapted to generate light of a second selected wavelength that is intensity modulated at the first frequency, the radiation being introduced to a subject at a second input port; the photodiode detector further adapted to detect alternately, at the detection port, light of the first and second wavelengths that have migrated in the tissue of the subject between the first and the second input ports and the detection port, respectively; the phase detector further adapted to receive alternately signals corresponding to the detected first and second wavelengths; and the processor further adapted to receive alternately phase shifts from the phase detector, the phase shifts being subsequently used for determination of the physiological property of the tissue.

The spectrophotometer may further include a second light source, operatively connected to the oscillator, adapted to generate light of a second selected wavelength that is intensity modulated at the first frequency, the radiation being introduced to a subject at a second input port; a second photodiode detector adapted to detect, at a second detection port, light of the second wavelength that has migrated in the tissue of the subject between the second input port and the second detection port, respectively; a second phase detector, operatively connected to receive a reference signal and a detection signal from the third diode detector, adapted to measure a phase shift between the introduced and the detected light at the second wavelength; and the processor further adapted to receive a second phase shift at the second wavelength, the first and second phase shifts being subsequently used for determination of the physiological property of the tissue.

The two wavelength spectrophotometer may further include a third light source, operatively connected to the oscillator, adapted to generate light of a third selected wavelength that is intensity modulated at the first frequency, the radiation being introduced to a subject at a third input port; a third photodiode detector adapted to detect, at a third detection port, light of the third wavelength that has migrated in the tissue of the subject between the third input port and the third detection port, respectively; a third phase detector, operatively connected to receive a reference signal and a detection signal from the third diode detector, adapted to measure a phase shift between the introduced and the detected light at the third wavelength; and the processor further adapted to receive phase shifts from the phase detector, the first second and third phase shifts being subsequently used for determination of the physiological property of the tissue.

The two or three wavelength spectrophotometer may further include a first, a second (or a third) magnitude detector connected to the first, second (or third) photodiode detectors, respectively, the magnitude detectors being adapted to measure magnitude of the detected light at each of the wavelengths; and the processor further adapted to receive the magnitudes for determination of the physiological property of the tissue.

The light source may be a light emitting diode for generating light of a selected wavelength in the visible or infra-red range.

The photodiode detector may be a PIN diode or an avalanche diode.

The examined physiological property of the tissue may be hemoglobin oxygenation, myoglobin, cytochrome iron and copper, melanin, glucose or other.

DESCRIPTION OF THE PREFERRED EMBODIMENTS

One preferred embodiment of the pathlength corrected oximeter utilizes three LEDs for generation of light at three selected wavelengths intensity modulated at a frequency of 50.1 MHz and coupled directly to the examined tissue. At each wavelength, the introduced light is altered by the tissue and is detected by a wide area photodiode placed against the skin. The introduced and detected radiations are compared to determine their relative phase shift that corresponds to an average pathlength of the migrating photons and, furthermore, the light attenuation is determined.

Figure 1:
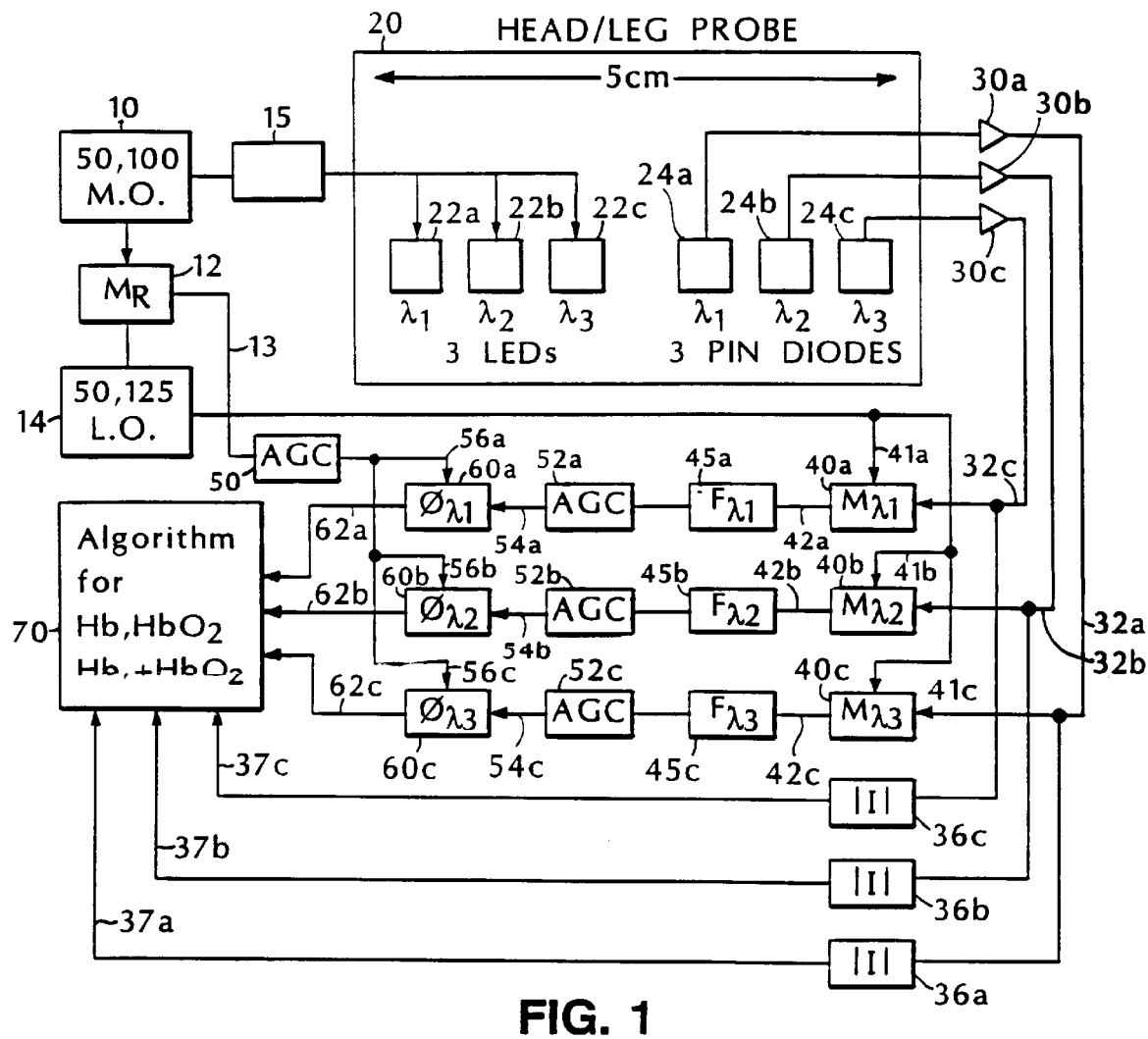
FIG. 1 is a block diagram of a pathlength corrected oximeter in accordance with the present invention.

Referring to FIG. 1, the oximeter includes a master oscillator 10 operating at 50.1 MHz connected to a power amplifier 15 of sufficient output power to drive LEDs 22a, 22b, and 22c (for example HLP 20RG or HLP 40RG made by Hitachi) that emit 760 nm, 840 nm, and 905 nm (or 950 nm) light, respectively. A second local oscillator 14 operating at 50.125 MHz and mixer 12 are used to generate a reference frequency 13 of 25 kHz. Each LED directly positioned on the skin has an appropriate heat sink to eliminate uncomfortable temperature increases that could also alter blood perfusion of the surrounding tissue. Three PIN diode detectors 24a, 24b, and 24c are placed at a distance of approximately 5 cm from the LEDs and have a detection area of about 1 $cm^2$. Photons migrating a few centimeters deep into the tissue are detected by the respective PIN diodes. The source-detector separation can be increased or decreased to capture deeper or shallower migrating photons. The signals from PIN diodes 24a, 24b, and 24c are amplified by preamplifiers 30a, 30b, and 30c, respectively.

The amplified signals (32a, 32b, 32c) are sent to magnitude detectors 36a, 36b, and 36c and to mixers 40a, 40b, and 40c, respectively. The magnitude detectors are used to determine intensity values of detected signals at each wavelength to be used in Eq. 1. Each mixer, connected to receive a 50.125 MHz reference signal (41a, 41b, 41c) from local oscillator 14, converts the detection signal to a 25 kHz frequency signal (42a, 42b, 42c). The mixers are high dynamic range frequency mixers, model SRA-1H, commercially available from Mini-Circuits (Brooklyn N.Y.). The detection signals (42a, 42b, and 42c) are filtered by filters 45a, 45b, 45c, respectively.

Phase detectors 60a, 60b, and 60c are used to determine phase shift between the input signal and the detected signal at each wavelength. Each phase detector receives the 25 kHz detection signal (54a, 54b, 54c) and the 25 kHz reference signal (56a, 56b, 56c), both of which are automatically leveled by automatic gain controls 50 and 52 to cover the dynamic range of signal changes. Phase detectors 60a, 60b, and 60c generate phase shift signals (62a, 62b, 62c) corresponding to the migration delay of photons at each wavelength. Each phase shift signal is proportional to the migration pathlength used in calculation algorithms performed by processor 70.

Figure 2:
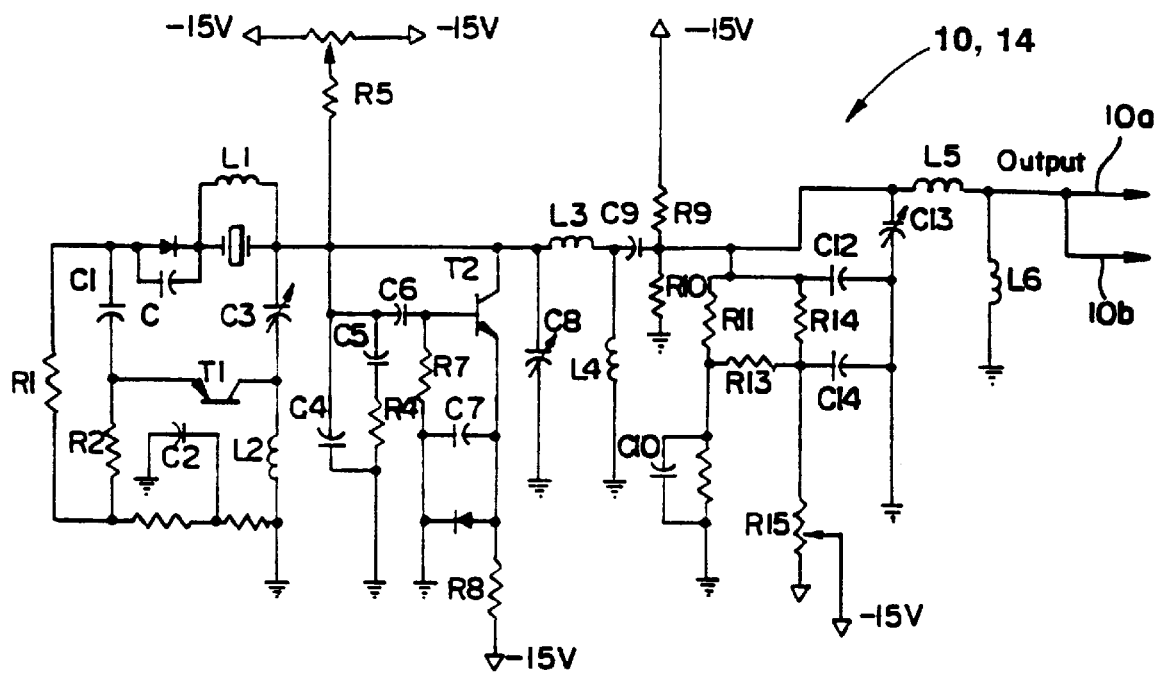
FIG. 2 is a schematic circuit diagram of a 50.1 MHz (50.125 MHz) oscillator used in the oximeter of FIG. 1.

FIG. 2 shows a schematic circuit diagram of a precision oscillator used as the 50.1 MHz master oscillator 10 and 50.125 MHz local oscillator 14. The oscillator crystals are neutralized for operation in the fundamental resonance mode; this achieves long-term stability. Both oscillators are thermally coupled so that their frequency difference is maintained constant at 25 kHz if a frequency drift occurs.

Figure 3:
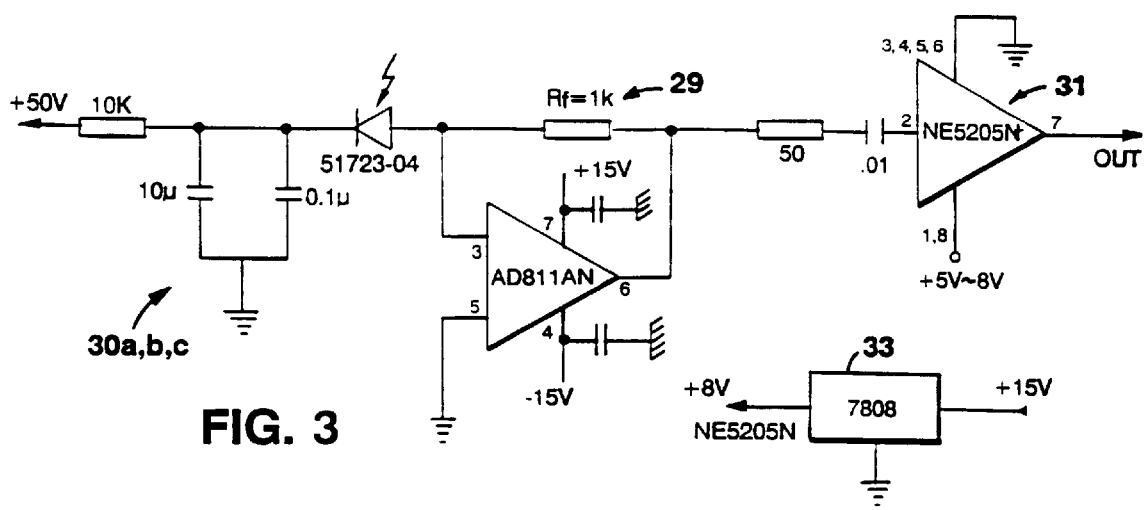
FIG. 3 is a schematic circuit diagram of a PIN diode and a preamplifier used in the oximeter of FIG. 1.
Figure 4:
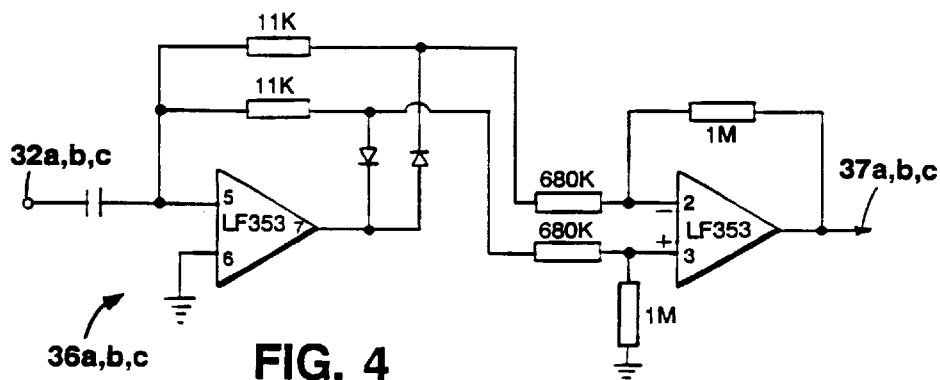
FIG. 4 is a schematic circuit diagram of a magnitude detector used in the oximeter of FIG. 1.

PIN diodes 24a, 24b, and 24c are directly connected to their respective preamplifiers 30a, 30b, and 30c, as shown in FIG. 3. The oximeter uses PIN silicon photodiodes S1723-04 with 10 mm×10 mm sensitive area and spectral response in the range of 320 nm to 1060 nm. The detection signal is amplified by stages 29 and 31, each providing about 20 dB amplification. The NE5205N operational amplifier is powered at +8V to operate in a high gain regime. The 8V signal is supplied by a voltage regulator 33. The amplified detection signals (32a, 32b, and 32c) are sent to magnitude detectors 36a, 36b, and 36c, shown in FIG. 4. The magnitude values (37a, 37b, and 37c) are sent to processor 70 that calculates the light attenuation ratio or logarithm thereof as shown Eq. 1.

Figure 5:
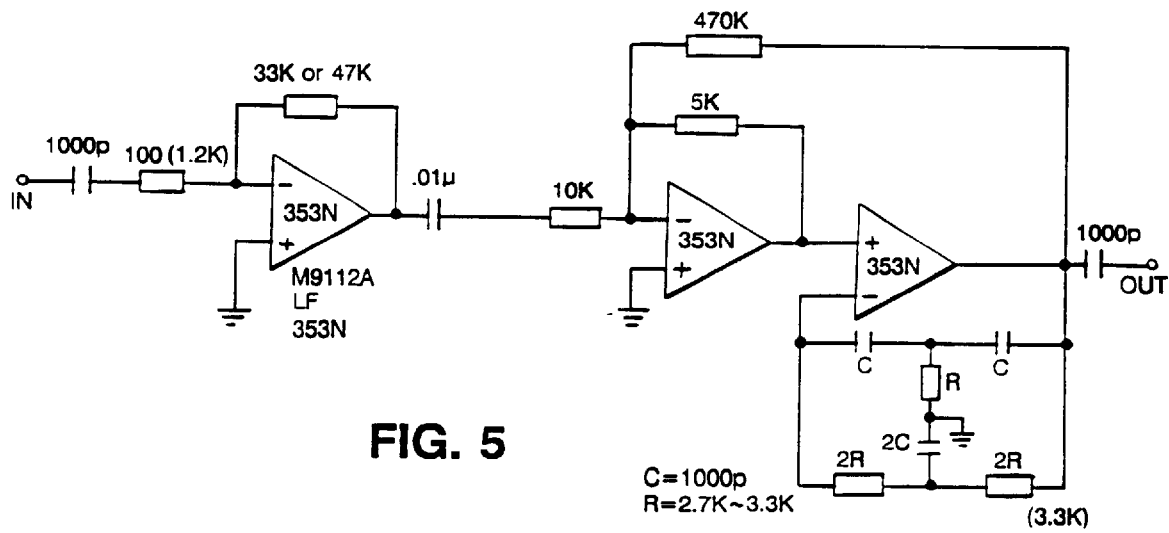
FIG. 5 is a schematic circuit diagram of a 25 kHz filter used in the oximeter of FIG. 1.

Also referring to FIG. 5, the AGC circuit uses MC 1350 integrated circuit for amplification that maintains the input signal of phase detector 60 at substantially constant levels. The amount of gain is selected to be equal for AGCs, 50 and 52. The signal amplitude is controlled by a feedback network 53. The AGCs provide a substantially constant amplitude of the detected and reference signals to eliminate variations in the detected phase shift due to cross talk between amplitude and phase changes in the phase detector.

Figure 6:
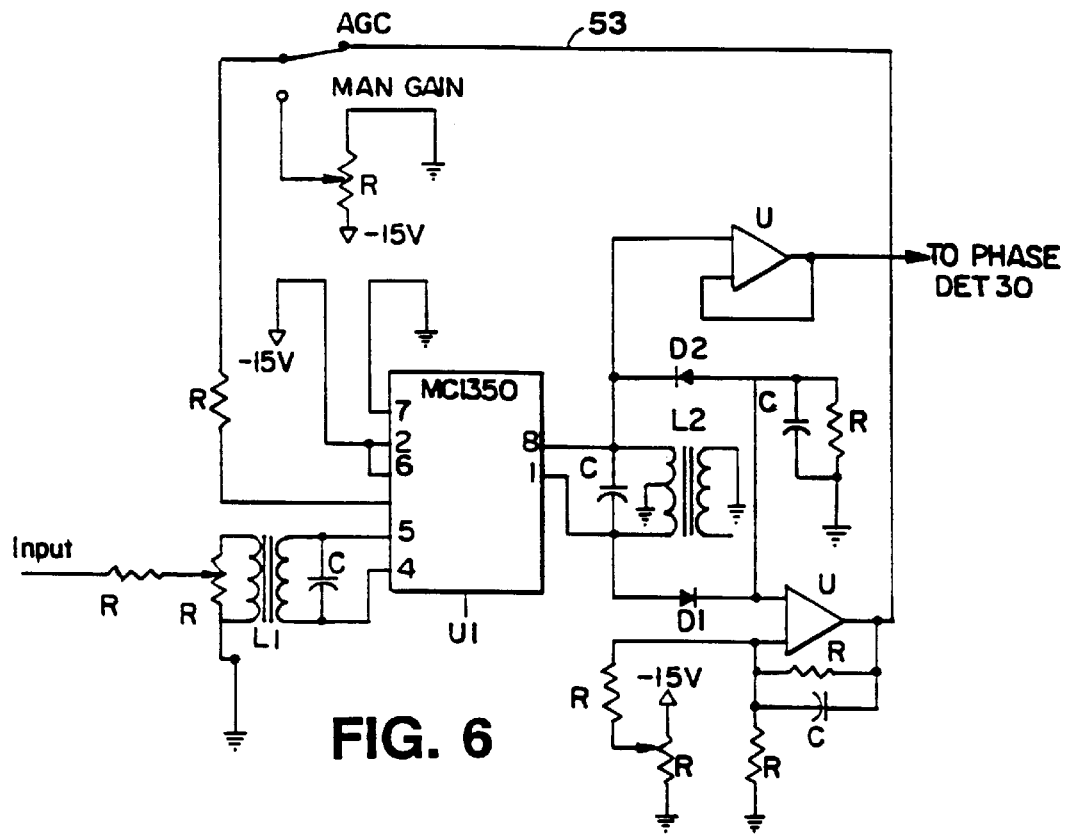
FIG. 6 is a schematic diagram of an AGC circuit of the oximeter of FIG. 1.
Figure 7:
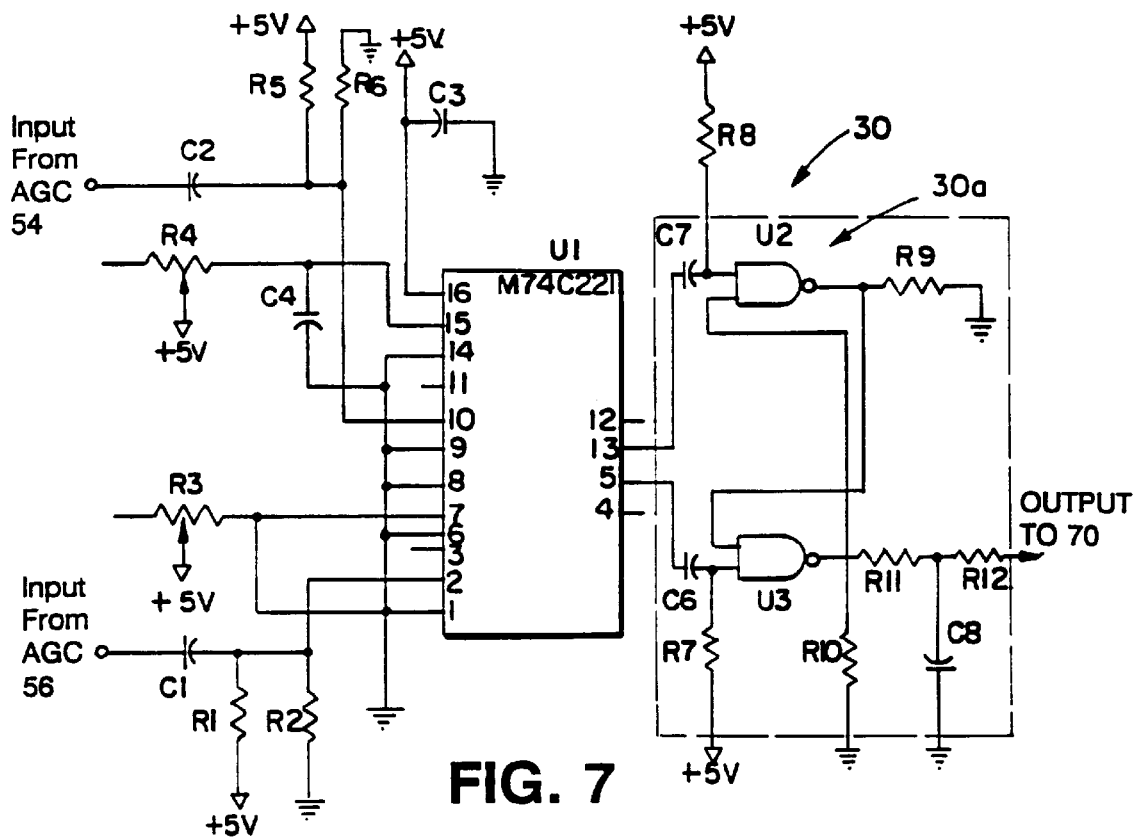
FIG. 7 is a schematic circuit diagram of a phase detector of the oximeter of FIG. 1.

Referring to FIG. 6, each phase detector includes a Schmitt trigger that converts the substantially sinusoidal detection signal (54a, 54b, 54c) and reference signal (56a, 56b, 56c) to square waves. The square waves are input to a detector that has complementary MOS silicon-gate transistors. The phase shift signal is sent to processor 70.

The oximeter is calibrated by measuring the phase shift for a selected distance in a known medium, i.e., using a standard delay unit, and by switching the length of a connector wire to change the electrical delay between master oscillator 10 and local oscillator 14.

Figure 8A:
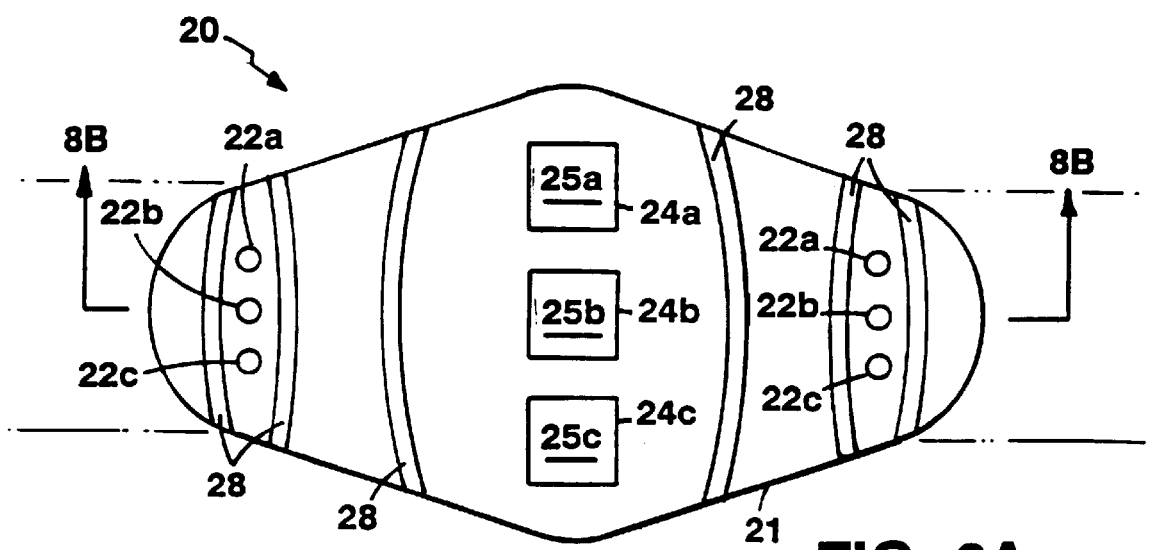
FIG. 8A is a plan view of a source-detector probe of the oximeter.
Figure 8B:
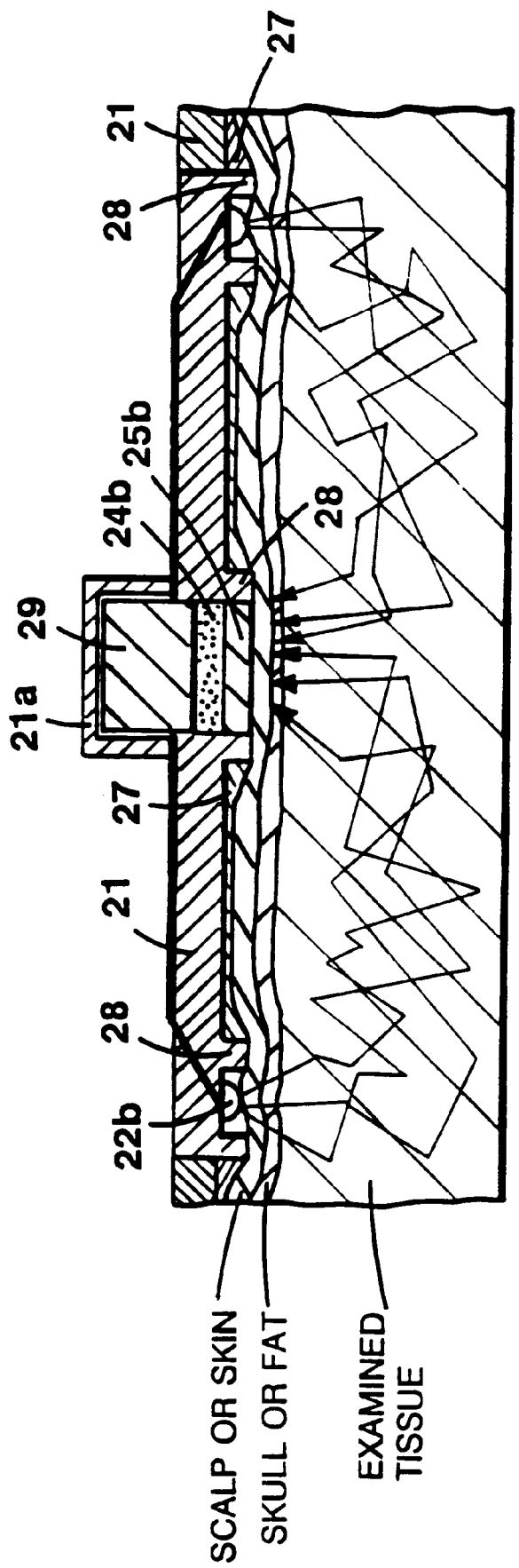
FIG. 8B is a transverse cross-sectional view taken on lines 8B of FIG. 8A further showing the photon migration.

Referring to FIGS. 8A and 8B source-detector probe 20 includes several LEDs (22a, 22b, 22c) of selected wavelengths and PIN photodiodes (24a, 24b, 24c) mounted in a body-conformable support structure 21. Structure 21 also includes a photon escape barrier 27 made of a material with selected scattering and absorption properties (for example, styrofoam) designed to return escaping photons back to the examined tissue. The support structure further includes a second conformable barrier 28, located between the LEDs and the diode detectors, designed to absorb photons directly propagating from the source to the detector and thus prevent detection of photons that migrate subcutaneously. Support structure 21 also includes electronic circuitry 29 encapsulated by an electronic shield 21a.

Each PIN diode is provided with an evaporated single wavelength film filter (25a, 25b, 25c). The filters eliminate the cross talk of different wavelength signals and allow continuous operation of the three light sources, i.e., no time sharing is needed.

The use of photodiode detectors has substantial advantages when compared with the photomultiplier tube used in standard phase modulation systems. The photodiodes are placed directly on the skin, i.e., no optical fibers are needed. Furthermore, there is no need to use a high voltage power supply that is necessary for the photomultiplier tube. The photodiodes are much smaller and are easy to place close to the skin. Advantages of the photomultiplier tube are a huge multiplication gain and a possibility of direct mixing at the photomultiplier; this cannot be achieved directly by a photodiode. This invention envisions the use of several different photodiodes such as PIN diode, avalanche diode, and other.

The processor uses algorithms that are based on equations described by E.M. Sevick et al. in "Quantitation of Time- and Frequency-Resolved Optical Spectra for the Determination of Tissue Oxygenation" published in Analytical Biochemistry 195, 330 Apr. 15, 1991 which is incorporated by reference as if fully set forth herein.

At each wavelength, the phase shift ($\theta^\lambda$) (62a, 62b, 62c) is used to calculate the pathlength as follows:

$$\theta^\lambda = \tan^{-1} \pi f \langle t^\lambda \rangle = \tan^{-1} 2\pi f \frac{\langle L^\lambda \rangle}{c} \approx \frac{2\pi f \langle L^\lambda \rangle}{c} \quad (2)$$

wherein f is modulation frequency of the introduced light which is in the range of 10 MHz to 100 MHz; $t^\lambda$ is the photon migration delay time; c is the speed of photons in the scattering medium; and $L^\lambda$ is the migration pathlength.

Equation (2) is valid at low modulation frequencies, i.e., $2\pi f \ll \mu_a \cdot c$. The modulation frequency of 50 MHz was selected due to the frequency limitation of the LEDs and photodiodes. However, for faster LEDs and photodiodes it may be desirable to use higher modulation frequencies that increase the phase shift. At high modulation frequencies, i.e., $2\pi f \gg \mu_a \cdot c$, the phase shift is no longer proportional to the mean time of flight <t>.

$$\theta^\lambda = a\rho\sqrt{(1-g)\mu_s f} \left\{1 - \frac{\mu_a^\lambda c}{4\pi f}\right\} \quad (3)$$

wherein $\rho$ is the source-detector separation; (1-g) $\mu_s$ is effective scattering coefficient; f is modulation frequency and $\mu_a^{80}$ is absorption coefficient at wavelength $\lambda$. At two wavelength, the ratio of absorption coefficients is determined as follows:

$$\frac{\mu_a^{\lambda_1}}{\mu_a^{\lambda_2}} = \frac{\theta^{\lambda_1} - \theta_0^{\lambda_1}}{\theta^{\lambda_2} - \theta_0^{\lambda_2}} \quad (4)$$

wherein $\theta_0^\lambda$ represents background scattering and absorption.

The wavelengths are in the visible and infra-red range and are selected to have absorbance sensitive (or insensitive) to various tissue components such as water, cytochrome iron and copper, oxy- and deoxygenated forms of hemoglobin, myoglobin, melanin, glucose and other.

For oxygenated and deoxygenated hemoblogin, the absorption coefficient written in terms of Beer Lambert relationship is as follows:

$$\mu_a^{\lambda_1} = \epsilon_{Hb}^{\lambda_1}[Hb] + \epsilon_{HbO}^{\lambda_1}[HbO_2] + \alpha^{\lambda_1} \quad (5)$$

wherein $\epsilon_{Hb}^{\lambda_1}$ and $\epsilon_{HbO}^{\lambda_1}$ are extinction coefficients for hemoglobin and deoxyhemoglobin that can be stored in a look up table; [Hb], [HbO$_2$] are the tissue concentration of hemoglobin and oxyhemoglobin, respectively; $\alpha^{\lambda_1}$ is background absorbance. The hemoglobin saturation is conventionally defined as follows:

$$Y = \frac{[HbO_2]}{[Hb] + [HbO_2]} \quad (6)$$

For a three wavelength measurement, the hemoglobin saturation can be calculated using Eqs. (5) and (6) as follows:

$$Y = \frac{a(\epsilon_{Hb}^{\lambda_3} - \epsilon_{Hb}^{\lambda_2}) - (\epsilon_{Hb}^{\lambda_1} - \epsilon_{Hb}^{\lambda_2})}{[(\epsilon_{HbO_2}^{\lambda_1} - \epsilon_{HbO_2}^{\lambda_2}) - (\epsilon_{Hb}^{\lambda_1} - \epsilon_{Hb}^{\lambda_2})] - a[(\epsilon_{HbO_2}^{\lambda_3} - \epsilon_{HbO_2}^{\lambda_2}) - (\epsilon_{Hb}^{\lambda_3} - \epsilon_{Hb}^{\lambda_2})]} \quad (7)$$

where $$a = \frac{\mu_a^{\lambda_1} - \mu_a^{\lambda_2}}{\mu_a^{\lambda_3} - \mu_a^{\lambda_2}}$$

Thus, processor 70 determines Y based on Eq. (7) using Eq. (2) to determine the average migration pathlength L that is then used in Eq. (1) and to determine $\mu_a^{80}$ for each wavelength $\lambda_1$, $\lambda_2$, $\lambda_3$.

In another embodiment, the spectrophotometer's electronics includes a low frequency module suitably and a high frequency module switchably coupled to the same source-detector probe 20. The low frequency module and the arrangement of the source-detector probe are substantially similar to the hemoglobinometer described in a copending U.S. patent application Ser. No. 701,127 filed May 16, 1991 which is incorporated by reference as if fully set forth herein. The low frequency module corresponds to a standard oximeter with modulation frequencies in the range of a few hertz to $10^4$ hertz and is adapted to provide intensity attenuation data at two or three wavelengths. Then, the LEDs are switched to the high frequency phase modulation unit, similar to the unit of FIG. 1, which determines the average pathlength at each wavelength. The attenuation and pathlength data are sent to processor 70 for determination of a physiological property of the examined tissue.

In another embodiment, the pathlength corrected oximeter utilizes the same LED sources (22a, 22b, 22c) sinusoidally modulated at a selected frequency comparable to the average migration time of photons scattered in the examined tissue on paths from the optical input port of the LED's to the optical detection part of the photodiode detectors (24a, 24b, 24c), but the electronic circuitry is different. The detector output is put through two wide band double balance mixers (DBM) which are coupled through a 90° phase splitter so that real (R) and imaginary (I) portions of the signal are obtained. The double balance mixers preferably operate at the modulation frequency. The phase ($\theta^\lambda$) is the angle whose tangent is the imaginary over the real part.

$$\theta^\lambda = \tan^{-1} \frac{I^\lambda}{R^\lambda} \quad (8)$$

The amplitude is the square root of the sum of the squares of these values, providing the phase shift has been taken out as the residual phase shift $\theta$ set to zero.

$$A^\lambda = \sqrt{(R^{80})^2 + (I^{80})^2} \quad (9)$$

This embodiment uses summing and dividing circuits to calculate the modulation index, which is the quotient of the amplitude over the amplitude plus the DC component obtained from a narrow band detector.

$$M^\lambda = \frac{A^\lambda}{A^\lambda + DC^\lambda} \quad (10)$$

The phase processor receives the phase shifts for the phase and amplitude values for two or three wavelengths and calculates the ratio of the phase shifts.

For each wavelength, the phase shift and the DC amplitude are used to determine a selected tissue property, e.g., hemoglobin oxygenation.

Additional embodiments are within the following claims:

What is claimed is:

1. A phase modulation spectroscopic apparatus comprising:
   an optical input port coupled to a light source and an optical detection port coupled to a detector, said input and detection ports being spaced several centimeters apart and arranged for spectroscopic examination of biological tissue;
   a modulator constructed to generate a modulation waveform with a first modulation frequency having a time characteristic compatible with the time delay of photon migration from said optical input port to said optical detection port in the biological tissue;
   said light source coupled to said modulator constructed to provide radiation of a first wavelength, said radiation being modulated at said modulation waveform and introduced into the tissue from said input port;
   said optical detector arranged to detect radiation of said first wavelength having photons that have migrated over migration paths in the examined tissue from said input port to said detection port; and
   a phase detector arranged to receive from said optical detector a detected waveform corresponding to said detected photons of said first wavelength and further arranged to compare said detected waveform with said modulation waveform and to determine therefrom a phase shift between said introduced and detected radiation at said first wavelength, said phase shift being indicative of scattering and absorptive properties of the examined tissue.

2. The apparatus of claim 1 further comprising
   a second light source optically coupled to said input port, said second light source being coupled to said modulator to provide a second wavelength of radiation being modulated at said modulation waveform having said first modulation frequency;
   said optical detector further constructed and arranged to detect radiation of said second wavelength having photons that have migrated over migration paths in the examined tissue from said input port to said detection port; and
   said phase detector further constructed and arranged receive a detected waveform corresponding to detected photons of said second wavelength and to compare said detected waveform with said modulation waveform to determine therefrom a phase shift at said second wavelength.

3. The apparatus of claim 1 wherein said light source is further constructed to provide a second wavelength of radiation being modulated at said modulation waveform having said first modulation frequency; said optical detector is further constructed and arranged to detect radiation of said second wavelength having photons that have migrated over migration paths in the examined tissue from said input port to said detection port; and said phase detector is further constructed and arranged receive a detected waveform corresponding to detected photons of said second wavelength and to compare said detected waveform with said modulation waveform to determine therefrom a phase shift at said second wavelength.

4. The apparatus of claim 3 wherein said light source is further constructed to provide a third wavelength of radiation being modulated at said modulation waveform having said first modulation frequency; said optical detector is further constructed and arranged to detect radiation of said third wavelength having photons that have migrated over migration paths in the examined tissue from said input port to said detection port; and said phase detector is further constructed and arranged receive a detected waveform corresponding to detected photons of said third wavelength and to compare said detected waveform with said modulation waveform and to determine therefrom a phase shift at said third wavelength.

5. The apparatus of claim 1, 2, 3 or 4 wherein said optical input and detection ports are arranged to be placed on the head of a subject.

6. The apparatus of claim 2, 3 or 4 wherein said wavelengths are selected to be sensitive to one or more constituents of the examined tissue.

7. The apparatus of claim 6 wherein one of said constituents is hemoglobin.

8. The apparatus of claim 6 wherein one of said constituents is cytochrome.

9. The apparatus of claim 2 or 3 further including a processor arranged to determine a ratio of said phase shifts determined at said two wavelengths.

10. The apparatus of claim 9 wherein said wavelengths are about 760 nm and 800 nm.

11. The apparatus of claim 9 wherein said processor is adapted to determine a concentration of hemoglobin in said tissue based on said ratio of phase shifts.

12. The apparatus of claim 1 wherein said modulator includes a single side band modulator.

13. The apparatus of claim 1 wherein said phase detector includes a lock-in amplifier.

14. The apparatus of claim 1 wherein said modulator and said phase detector include first transceiver for generating said waveform of said first modulation frequency and second transceiver for receiving said detected waveform from said detector and receiving said modulation waveform from said first transceiver thereby being in a phase locked loop, and a lock-in amplifier for providing said phase shift.

15. The apparatus of claim 1 wherein said first and second transceivers are constructed to operate in a single sideband mode.

16. The apparatus of claim 1 wherein said modulator is constructed to provide said modulation waveform of a second frequency in the range of 144 MHz to 500 MHz; said light source is constructed to provide radiation being modulated at said modulation waveform having said second modulation frequency; said optical detector is constructed and arranged to detect said optical radiation modulated by said waveform of said second modulation frequency, photons of said detected radiation have migrated over migration paths in the examined tissue from said input port to said detection port; and said phase detector is constructed and arranged to receive a detected waveform corresponding to detected photons and to compare said detected waveform with said modulated waveform having said second frequency to determine therefrom a phase shift between said introduced and detected radiation modulated at said second modulation frequency.

17. The apparatus of claim 1 further including a processor adapted to provide an indication of scattering and absorptive properties of the examined tissue from said phase shift.

18. The apparatus of claim 1 further including a processor arranged to calculate, based on said phase shift, an optical pathlength of photon migration between said input and detection ports.

19. The apparatus of claim 18 wherein said optical input and detection ports are arranged to be placed on the head of a subject and said optical pathlength is employed to determine brain bleeding.

20. The apparatus of claim 1 wherein said modulator is constructed to generate said first modulation frequency in the range of 144 MHz to 500 MHz.

21. The apparatus of claim 20 wherein said modulator provides said first modulation frequency selected based on a separation of said optical input and detection ports.

22. The apparatus of claim 1 wherein said wavelength is visible or near infrared wavelength.

23. The apparatus of claim 22 wherein said phase detector is constructed to provide the amplitude of said detected waveform.

24. The apparatus of claim 23 including a processor adapted to provide changes in hemoglobin concentration from the amplitude of the detected signal.

25. A spectroscopic apparatus for examination of biological tissue with one or more constituents having specific concentrations and having a quantifiable parameter associated with a particular wavelength of electromagnetic radiation, said apparatus comprising:

a first light source constructed to introduce first electromagnetic radiation into the tissue at an optical input port;

a first optical detector arranged to detect said first electromagnetic radiation having photons that have migrated over migration paths in the examined tissue from said input port to a detection port, said first detector providing a detection signal corresponding to the intensity of said detected first radiation;

a circuitry connected to receive said detection signal from said first detector and arranged to determine intensity of radiation absorbed due to at least one of said constituents; and an optical system including a second light source constructed to introduce second electromagnetic radiation into the tissue at said optical input port, and a second detector arranged to detect said second electromagnetic radiation having photons that have migrated over migration paths in the examined tissue from said input port to said detection port, said optical system being arranged to determine an optical pathlength of photon migration in the examined tissue between said optical input and detection ports to evaluate a change in concentration of at least one constituent of the tissue.

26. The apparatus of claim 25 wherein said optical system is a phase modulation spectrophotometer.

27. The apparatus of claim 26 wherein said phase modulation spectrophotometer includes a modulator constructed to generate a modulation waveform with a modulation frequency having a time characteristic compatible with the time delay of photon migration from said optical input port to said optical detection port in the biological tissue; said second light source being coupled to said modulator to provide a first wavelength of said second electromagnetic radiation being modulated at said modulation waveform having said modulation frequency; said second optical detector being constructed and arranged to detect said second radiation of said first wavelength having photons that have migrated over migration paths in the examined tissue from said input port to said detection port, and said phase modulation spectrophotometer further including a phase detector constructed and arranged receive a detected waveform from said second detector and to compare said detected waveform with said modulation waveform to determine therefrom a phase shift.

28. The apparatus of claim 25, 26 or 27 wherein said second light source and said second optical detector are arranged to emit and detect said first electromagnetic radiation of two wavelengths.

29. The apparatus of claim 25 wherein one of said constituents is hemoglobin.

30. The apparatus of claim 25 wherein one of said constituents is cytochrome.

31. The apparatus of claim 25 wherein said optical input and detection ports are arranged to be placed on the head of a subject for examination of brain tissue.

32. The apparatus of claim 25 wherein said first light source is constructed to emit radiation having a spectrum of wavelengths.

33. The apparatus of claim 32 wherein said first light source includes a light bulb.

34. The apparatus of claim 25 wherein said first light source and said first optical detector are respectively arranged to emit and detect said first electromagnetic radiation of two wavelengths.

35. The apparatus of claim 34 wherein said two wavelengths are about 760 nm and about 800 nm.

36. The apparatus of claim 34 wherein said two wavelengths are in the visible to near infrared range.

* * * * *